United States Patent [19]

Curbelo

[11] Patent Number: 5,262,635
[45] Date of Patent: Nov. 16, 1993

[54] TECHNIQUES FOR CORRECTING NON-LINEARITY IN A PHOTODETECTOR USING PREDEFINED CALIBRATION INFORMATION

[75] Inventor: Raul Curbelo, Lexington, Mass.

[73] Assignee: Bio-Rad Laboratories, Inc.

[21] Appl. No.: 882,184

[22] Filed: May 12, 1992

Related U.S. Application Data

[63] Continuation-in-part of Ser. No. 795,361, Nov. 20, 1991, abandoned.

[51] Int. Cl.[5] ............................................. H01J 40/14
[52] U.S. Cl. ............................ 250/214 R; 250/214 A
[58] Field of Search ............ 250/214 C, 214 R, 214 A; 356/346, 351; 364/575, 574, 498

[56] References Cited

U.S. PATENT DOCUMENTS

| | | | |
|---|---|---|---|
| 2,948,815 | 8/1960 | Willems et al. | 250/211 |
| 4,323,309 | 4/1982 | Akitomo et al. | 364/498 |
| 4,673,812 | 6/1987 | Yoneda | 250/339 |
| 4,682,022 | 7/1987 | Hoult et al. | 250/214 A |
| 4,724,315 | 2/1988 | Goerne | 250/214 A |
| 4,744,657 | 5/1988 | Aralis et al. | 364/498 |
| 4,864,120 | 9/1989 | Van Der Laak et al. | 250/214 A |
| 4,927,269 | 5/1990 | Keens et al. | 356/346 |

OTHER PUBLICATIONS

Technical Support Package on "Correcting for Nonlinearity in a Photodetector" for *NASA Tech Brief*, vol. 10, No. 2, Item #152 from JPL Invention Report NPO-16055/5509, Inventor: R. A. Schindler, Prepared by: R. S. Jamieson, TSP assembled by: JPL Technology Utilization Office, pp. i, 1–4, Mar. 1986.

*Primary Examiner*—David C. Nelms
*Assistant Examiner*—Que T. Le
*Attorney, Agent, or Firm*—Townsend and Townsend Khourie and Crew

[57] ABSTRACT

A technique that corrects photodetector non-linearity without increasing the noise level in the detector signal. The detector is coupled to a preamplifier characterized by the absence of positive feedback, and the preamplifier signal is communicated to a linear amplifier whose output signal is then digitized. The digitized signal is then transformed according to stored calibration information that is representative of the non-linear characteristic of the photodetector. The transformed digitized value thus exhibits a linear characteristic as a function of the intensity of the light source. A number of embodiments perform the correction in hardware before digitizing the signal.

28 Claims, 6 Drawing Sheets

TECHNIQUES FOR CORRECTING NON-LINEARITY IN A PHOTODETECTOR USING PREDEFINED CALIBRATION INFORMATION

The application is a continuation-in-part of a patent application Ser. No. 07/795,361 filed Nov. 20, 1991, now abandoned.

BACKGROUND OF THE INVENTION

The present invention relates generally to photodetectors and more specifically to techniques for providing a linear detector output for use in a Fourier transform spectrometer.

A Fourier transform spectrometer typically includes a Michelson interferometer into which an infrared beam to be analyzed and a monochromatic reference beam (typically in the visible range) beam are directed. The interferometer has a fixed mirror and a movable mirror which is driven at a nominally constant velocity over a portion of its travel. Each of the input beams is split at a beam splitter with one portion traveling a path that causes it to reflect from the fixed mirror and another portion traveling a path that causes it to reflect from the movable mirror. The portions of each beam recombine at the beam splitter, and the recombined infrared and monochromatic beams are directed to appropriate photodetectors (detectors).

Due to optical interference between the two portions of each beam, the intensity of the monochromatic beam is modulated at a frequency proportional to its optical frequency and the mirror velocity while each frequency component of the infrared beam is modulated at a frequency proportional to that component's optical frequency and the mirror velocity.

Each detector has associated circuitry to generate a voltage representative of (preferably proportional to) the light intensity falling on the detector. The infrared detector output signal therefore represents the superposition of the modulated frequency components and provides an interferogram whose Fourier transform yields the desired spectrum. The monochromatic detector provides a nominally sinusoidal reference signal whose zero crossings occur each time the moving mirror travels an additional one quarter of the reference wavelength. The data acquisition electronics are triggered on these zero crossings to provide regularly sampled values for the interferogram. With the appropriate choice of mirror velocity, the output signal can be made to fall within a convenient range of modulation frequencies, as for example in the audio range.

Certain types of detectors, such as photodiodes and photomultiplier tubes are typically used with DC amplifiers, while others, such as photoconductors are typically used with AC amplifiers. In either case, the average value of the interferogram provides no useful spectral information, and is typically subtracted out before performing the Fourier transform.

The interferogram is characterized by a centerburst region of very large intensity fluctuations, corresponding to the portion of the mirror travel where the two optical path lengths in the interferometer are equal. The centerburst need not be at the center of the interferogram since the mirror need not be scanned equal distances on either side. A technique called gain ranging is sometimes used to lower the amplifier gain in the centerburst region.

One type of infrared detector comprises a photoconductive material such as mercury cadmium tellurium (MCT). A photoconductive material has a conductivity that varies with the luminous flux falling on the material. The ideal photoconductor would have a linear characteristic, so that when it is biased with a constant voltage, the current through it would vary linearly with the intensity. It is well known to use negative feedback in the preamplifier to provide an output voltage that is a direct measure of the detector current.

The real-world photoconductor is not linear, however, but rather exhibits non-linear behavior that to some extent approximates that of an ideal photoconductor in series with a fixed resistance. In the context of a Fourier transform spectrometer, the non-linearity in the detector output signal manifests itself by distorting the resultant spectrum in the wavelength regions where the detector is sensitive, and producing artifacts indicating the presence of energy in wavelength regions where the detector is actually insensitive. A typical approach is to accept the non-linearity as inevitable, and operate in a range of low infrared source intensity where the detector characteristic is approximately linear. This is sometimes undesirable, however, since a greater source intensity would improve the signal-to-noise ratio of the spectral measurement.

It is also known to correct the non-linearity by providing positive feedback in the preamplifier circuit so as to balance out the non-linear effect of the internal series resistance. While the positive feedback approach is presumably effective in correcting the detector non-linearity, the use of positive feedback will increase the effective noise of the amplifier. This is not a problem for relatively noisy detectors where the detector noise (as opposed to the amplifier noise) is the limiting factor in the overall signal-to-noise ratio. However, current state of the art detectors are characterized by low noise; therefore, amplifier noise becomes a performance-limiting factor. For example, if the detector noise is only on the order of twice the preamplifier noise, the effect of positive feedback in the preamplifier will be to raise the preamplifier noise to the same level as the detector noise.

SUMMARY OF THE INVENTION

The present invention provides a technique that corrects photodetector non-linearity without increasing the noise level in the detector signal. As a result of the correction, it is possible to operate a spectrometer at higher source intensity and thereby benefit from improved signal-to-noise ratio.

In one set of embodiments, the detector is coupled to a linear amplifier system whose output signal is digitized and corrected according to stored calibration information that is representative of the non-linear characteristic of the photodetector. The corrected digitized values thus exhibit a linear characteristic as a function of the intensity of the light source. In some embodiments, the correction is applied before the digitization; in others, after.

It is preferred, at least from an accuracy point of view, to correct each sampled measured voltage in the interferogram by an amount appropriate for that measured voltage. This requires a knowledge of the actual voltage (AC and DC components). In specific implementations, this is provided by separate AC and DC amplifiers.

Where the correction is performed in software, the calibration information may be stored as one or more numerical parameters for an analytical formula, which can be evaluated for each measured voltage. It is often possible to approximate the detector's non-linearity by a single numerical parameter representing a fixed internal series resistance. Table lookup techniques may also be used.

Where the correction is performed in hardware, the calibration information is embodied in a non-linear network. In one set of embodiments the non-linear network includes diodes and resistors; in another it includes an A/D converter, a ROM-based lookup table, and a D/A converter. The non-linear network may be used to correct the voltage directly, or may be used to provide a correction signal. In the latter case, a voltage representing the correction factor is generated by communicating a voltage representing the total intensity through a non-linear network, and the AC voltage is multiplied by this factor. The multiplication can be effected using a gain-controlled amplifier following the AC preamplifier.

A different hardware approach utilizes positive feedback to perform the correction, but in the amplifier rather than the preamplifier. This avoids the problem of the prior art technique, since the noise introduced by the positive feedback is now a small fraction of the preamplified detector noise.

A preferred calibration procedure entails taking voltage measurements for various known levels of source intensity or at various levels of source intensity having a known relationship to each other. This may be done by acquiring interferograms at the various intensity levels. Performing the calibration in the interferometer is advantageous since it takes into account any amplifier non-linearity as well as detector non-linearity.

A number of simpler alternative embodiments provide meaningful, but less precise, correction. For example, the maximum peak-to-peak excursions of the interferogram (as measured with an AC amplifier) provide information regarding the interferograms average value (based on assumptions regarding the interferometer's chopping efficiency). Thus, it is possible to perform a point-by-point correction based on the approximate derived average value without a separate DC amplifier. A further approach along this line is to use the same correction factor, determined by the average value, for all points. This avoids the need to provide a wideband DC-coupled amplifier.

A further understanding of the nature and advantages of the present invention may be realized by reference to the remaining portions of the specification and drawings.

DESCRIPTION OF SPECIFIC EMBODIMENTS

Prior Art Detector Signal Generation (DC-Coupled)

Figure 1A:
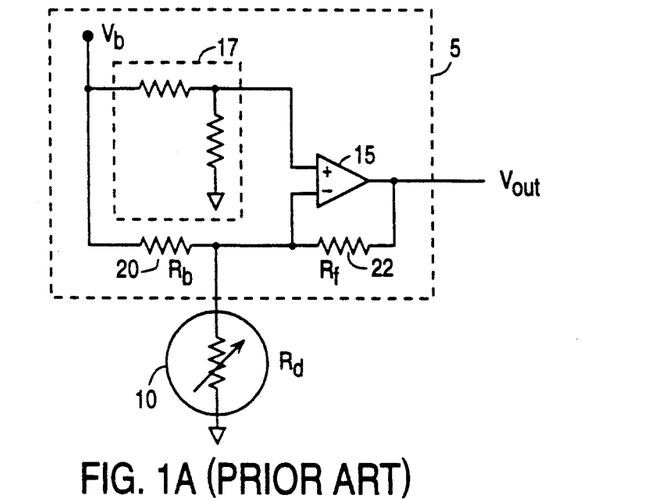
FIG. 1A is a simplified circuit schematic of a representative prior art DC-coupled preamplifier and photodetector circuit.

FIG. 1A is a simplified circuit schematic of a prior art preamplifier stage for a photodetector 10. The preamplifier stage does not provide correction for detector non-linearity. The particular preamplifier shown is DC-coupled.

Detector 10 has a first terminal coupled to the inverting input terminal of an operational amplifier 15 and also through a bias resistor 17 to a supply voltage $V_b$. The detector has a second terminal connected to ground. A voltage divider 20 maintains the non-inverting input terminal of the amplifier at a constant voltage $V_d$ which is a predetermined fraction of the supply voltage $V_b$.

Negative feedback is provided by a feedback resistor 22 coupled between the amplifier's inverting input terminal and output terminal. This holds the voltages at the non-inverting and inverting input terminals at substantially the same level. Thus, the first terminal of detector 10 is held at the same constant voltage $V_d$ defined by voltage divider 17, and the output voltage $V_{out}$ is given as follows:

$$V_{out} = (V_d R_f) G_d + [V_d + G_b R_f (V_d - V_b)] \qquad (1)$$

where $G_d$ = conductance of detector ($1/R_d$);
$R_f$ = resistance of feedback resistor; and
$G_b$ = conductance of bias resistor ($1/R_b$).

Thus, it can be seen that $V_{out}$ is a linear function of the photodetector conductance. To the extent that the photodetector conductance is proportional to the intensity of the radiation falling on the detector, the output voltage $V_{out}$ is a linear function of the intensity.

However, it is known that the conductance of a typical photodetector is not proportional to the intensity, and thus the output voltage is a non-linear function of intensity. Although a number of factors contribute to the non-linearity, a simple model treats the photoconductor as an ideal photoconductor in series with a first fixed resistor, the series combination being in parallel with a second fixed resistor. As will be seen below, this model predicts a particular analytical form of the intensity dependence.

Figure 1B:
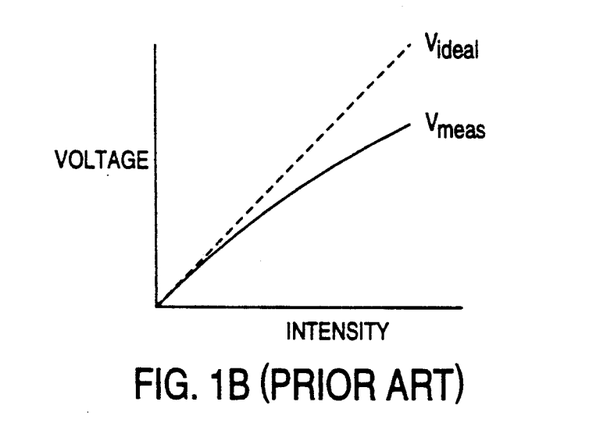
FIG. 1B is a typical plot showing the non-linear detector response.

FIG. 1B shows a typical non-linear detector response, where the measured voltage ($V_{meas}$) is plotted as a function of intensity. The ideal linear response $V_{ideal}$ is shown as a dashed line. In this plot, the voltages have been offset so that they are zero for zero intensity.

Software Correction—Data Acquisition and Analysis System

Figure 2:
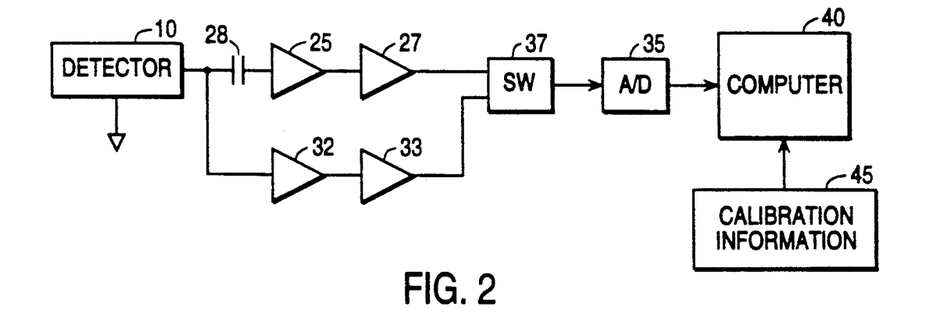
FIG. 2 is a block diagram of an embodiment of the invention where the correction is done in software.

FIG. 2 is a block diagram of the data generation and acquisition system incorporating the detector non-linearity correction in a preferred embodiment of the present invention. This will be described in the context of operating a Fourier transform spectrometer where the detector signal is amplified, sampled and digitized, and subjected to numerical processing.

In many prior art spectrometers, and in most using MCT detectors, the preamplifier and amplifier are AC-coupled, since there is no need for zero-frequency spectral information. Indeed, any residual average value of the interferogram (resulting from amplifier imperfections and inherent digitization error in the A/D converter) is normally subtracted out prior to the Fourier transform operation. Thus, the measured interferogram voltage values contain limited information on the average value of the light intensity.

As will be discussed below, the calibration and correction of the detector non-linearity require knowledge of the AC and DC components of the detector voltage. While this might militate toward use of a DC amplifier, a number of factors favor a different approach. For example, a photoconductive detector typically provides an output voltage having a large DC value for zero light intensity. If the detector were coupled to a DC amplifier as shown in FIG. 1A with $R_b$ an open circuit, the signal for a typical interferogram might be characterized by (a) noise having amplitudes in the subnanovolt range; (b) an AC signal component having amplitudes ranging between nanovolts (away from the centerburst) and up to a fraction of a volt (near the centerburst); and (c) a DC component generally proportional to the average intensity of about 1 volt. However, this is superimposed on a DC level for zero intensity on the order of 5–10 volts. A typical A/D converter provides a full range of output for an input range of about 10 volts. If the digitization were applied to the entire signal, the AC component of interest would only span about 10% of the A/D range, and thus would be digitized very coarsely.

While it is possible to select a value for $R_b$ that would provide an output voltage of zero volts for zero intensity, a DC-coupled amplifier still represents a non-optimum way to measure the AC signal in this application. DC-coupled amplifiers are prone to DC drift, and attempts to optimize them for low drift tend to add noise and degrade their AC performance. Accordingly, the presently preferred embodiment, which will be outlined and described in detail below, includes separately optimized AC-coupled and DC-coupled amplifier channels with the AC-coupled channel optimized for low noise, the DC-coupled channel optimized for low drift, and the gains tailored for full use of the A/D converter range. Since the dual-channel approach adds a level of complexity, a DC-coupled amplifier having low noise and low drift might be preferred, if such a device were available at a reasonable cost.

The AC channel includes a linear preamplifier 25 and a linear amplifier 27 (which is optional). While the prior art shows the use of positive feedback in the preamplifier in order to correct the detector non-linearity, the preamplifier used in connection with the present invention is characterized by the absence of positive feedback. The fact that this channel is AC-coupled is denoted schematically by the presence of a blocking capacitor 28 at the input to the preamplifier. The signal from amplifier 27 is the raw interferogram from which the ultimate spectrum will be derived.

The DC channel includes a linear DC preamplifier 32 and a linear DC amplifier 33 (optional), which are optimized for low drift. The DC channel, whose function is to provide the average value of the interferogram, is characterized by a small bandwidth (say on the order of 0–100 Hz). This bandwidth may extend to the low-frequency cutoff of the AC channel. The non-zero frequencies in the DC channel are outside frequencies in the spectral range of interest but may contain information needed for the correction.

The analog voltage from amplifier 27 is communicated to an A/D converter 35 having associated sample and hold circuitry. In a typical device the analog voltage signal is sampled and digitized for each zero crossing of the monochromatic reference signal as the mirror moves over a designated portion of its range of travel. The voltage from amplifier 33 is also communicated to A/D converter 35, and is sampled at one or more points in the scan when the interferogram points are not being sampled. This could be in between samples, at either both ends of the scan, at some point during the mirror retrace, or during a special DC measuring scan. A switch 37 determines which amplifier output is communicated to the A/D converter. Alternatively, the A/D converter could be provided with separate sample and hold circuits for the AC and DC channels, with both values being digitized at every sample point.

The digitized values of the voltages are communicated to a computer 40 for further processing. Computer 40 executes a program, to be described below, that calculates a spectrum based on the digitized interferogram data points. Associated with the processing software is stored calibration information, shown as a separate block 45, that is used to correct the data points to account for detector non-linearity as will be discussed in greater detail below. It should be understood that the computer also controls the operation of the spectrometer.

Figure 3:
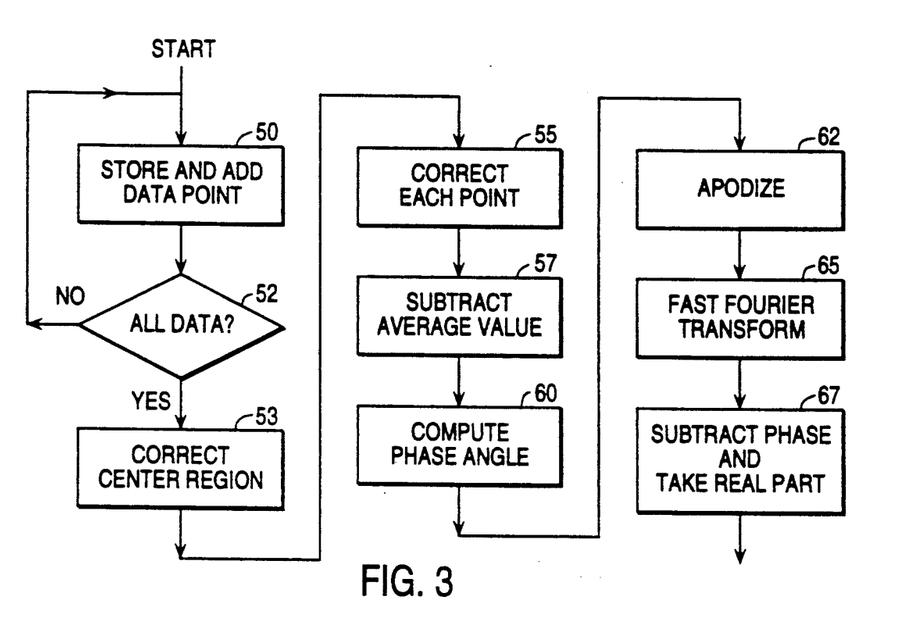
FIG. 3 is a flow diagram of the processing and correction program for carrying out the software correction.

FIG. 3 is a flow diagram of the program executed by the computer to convert the interferogram to a spectrum. As single data points are generated, they are stored and co-added (step 50). It is a standard practice to average a number of interferograms. Thus, upon acquiring each data point, the computer tests (step 52) whether all the data points for the requisite number of interferograms have been accumulated. If not, the computer causes further data points to be acquired. Once all the interferograms have been accumulated and averaged, the computer corrects (step 53) the center region of the interferogram to compensate for the fact that a gain-ranging amplifier was used. To the extent that gain-ranging is not used, this step would not be performed.

Each point in the interferogram is then corrected (step 55) to compensate for detector non-linearity. This correction step will be described in detail below. The average value of the interferogram (the average of all the corrected points) is then subtracted from each point (step 57) and the shifted interferogram stored. A phase angle is then computed (step 60) by performing a Fourier transform on a small region centered on the centerburst.

The interferogram is then apodized (step 62) and subjected to a Fourier transform (step 65) to provide a complex spectrum. The computed phase angle from step 60 is subtracted, leaving a resultant complex spectrum, and the real part is extracted (step 67) to provide the output spectrum.

As noted above, this embodiment is not DC-coupled, but rather develops the signals required for calibration and correction through the use of separate AC and DC channels. This requires a measurement of the relative gains in the two channels so that the AC and DC voltage information can be properly correlated.

Figure 4:
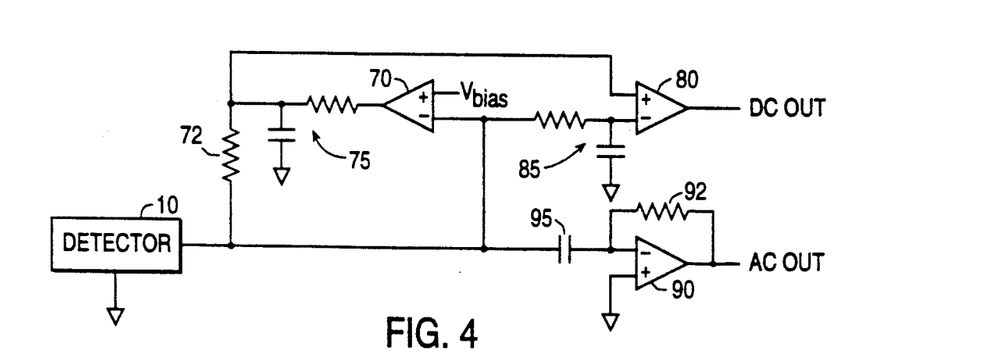
FIG. 4 is a simplified circuit schematic of a preferred embodiment of the preamplifier and detector circuit with separate AC and DC channels.

FIG. 4 is a somewhat simplified schematic of detector 10 and its associated biasing circuitry, along with preamplifier circuitry for the AC and DC channels. The biasing circuitry includes an operational amplifier 70 and a bias resistor 72 (on the order of 100Ω to 1K). Amplifier 70 has its non-inverting input terminal held at a constant DC voltage $V_{bias}$ and its inverting input terminal coupled to detector 10. Thus amplifier 70 operates to maintain a constant bias voltage on the detector. A filter network 75 filters the noise output from amplifier 70.

A DC amplifier 80 has its input terminals coupled across bias resistor 72, while a filter network 85 at the inverting input terminal filters the AC signal component of the detector current (the filter cutoff is chosen to provide the desired bandwidth for the DC channel). Thus amplifier 80 provides a DC voltage proportional to the DC component of the detector current. An AC amplifier 90 with a feedback resistor 92 (on the order of 10K) has its inverting input terminal coupled through a capacitor 95 to the detector, and provides an AC voltage proportional to the AC component of the detector current.

The amplifier gains are selected so that the AC and DC voltages are appropriately scaled for the A/D converter. That is, the AC component should have peak-to-peak voltages of a few to several volts, and the DC component should also be a few to several volts. For the example discussed above, the AC component is about an order of magnitude smaller than the DC component for the same amplification. Therefore, it is appropriate to set the circuit parameters for an AC gain about 10 times the DC gain.

For the schematic shown, the AC output voltage for a given intensity is the product of the value of the feedback resistor and the AC current component, while the DC output voltage is the product of the value of the bias resistor and the DC current component (assuming unity gain for amplifier 80). The appropriate gains can thus be achieved by selecting appropriate resistance values of these circuit components.

As mentioned above, it is necessary to know precisely the relative scaling between the AC and DC channels, which can be determined in a number of ways. One way is to calculate the scaling on the basis of the known circuit parameters as described above. Another way is to measure the DC output voltage through the DC channel for zero intensity and for illumination at a certain constant intensity level, and then to chop the constant intensity illumination and measure the AC output voltage through the AC channel. If $V_0$ and $V_1$ are the DC output voltages and $V_2$ is the peak-to-peak value of the AC output voltage, the ratio of the scale factors is given by $V_2/(V_1-V_0)$. The constant intensity used for the relative scaling calibration should be low enough that the detector nonlinearity does not come into play.

Calibration and Correction (DC-Coupled)

As noted above, the detector preamplifier output voltage (and therefore the amplifier output voltage) is a linear function of the detector conductance, but the detector conductance is not simply proportional to intensity. For purposes of illustration, the detector will be considered to be an ideal photoconductor in series with a fixed resistance, with the series combination in parallel with another fixed resistance. Moreover, it will be assumed that the preamplifier and amplifier are DC-coupled. In this simplified model, the detector conductance is given by:

$$G=(G_{ideal}/(1+R_sG_{ideal}))+1/R_p \quad (2)$$

where
$G_{ideal}$ = conductance of the ideal photoconductor;
$R_s$ = fixed series resistance; and
$R_p$ = fixed parallel resistance.

Since $G_{ideal}$ is proportional to the input optical power P, the measured voltage $V_{meas}$ is given by:

$$V_{meas}=baP/(1+R_saP)+V_0 \quad (3)$$

where
a = proportionality factor between conductance and input optical power;
b = proportionality factor between amplifier output voltage and detector conductance; and
$V_0$ = voltage for zero input optical power.

The inverse of Equation 3 then becomes:

$$P=(V_{meas}-V_0)/(ba-R_sa(V_{means}-V_0)) \quad (4)$$

A linear detector would provide a "correct" voltage $V_{corr}=baP+V_0$ so that $V_{corr}$ in terms of $V_{meas}$ is given by:

$$V_{corr}=baP+V_0=(V_{meas}-V_0)/(1-\alpha(V_{meas}-V_0))+V_0 \quad (5)$$

where
$\alpha=R_s/b$.

Thus, for this simplified model, the correction is characterized by a parameter $\alpha$ that characterizes the non-linearity and the voltage $V_0$ that corresponds to zero intensity. To the extent that the light intensity is varying, the amplifier must have the same gain at zero frequency and over the range of frequencies that characterize the intensity variations. If such is the case, the measured voltage at any instant can be corrected as set forth in Equation 5. However, if the DC and AC gains are different, different proportionality factors apply, and the simple form of correction does not apply.

The calibration procedure entails making a number of voltage measurements at different levels of intensity of detector illumination, including at least some intensity levels that are high enough that the detector exhibits non-linear behavior. If the detector channel is DC-coupled, the calibration can be performed by illuminating the detector with a source of adjustable but otherwise fixed intensity, and making direct measurements of the output voltage for different values of intensity. The source intensity adjustment can be achieved by using a black body source and controlling the temperature, or by using a fixed intensity source with one or more attenuators having known characteristics.

If the non-linearity correction is characterized by a pair of parameters in a known functional relationship (such as $\alpha$ and $V_0$ in Equation 5), it is theoretically possible to determine these parameters based on a voltage measurement at zero intensity and two voltage measurements at non-zero intensities differing by a known ratio, even if the absolute intensity values are not known. Moreover, if a second pair of measurements is taken with different intensities, it may not even be necessary to know the intensity ratio, so long as the same ratio is used for both pairs. In any event, the measurement is inherently subject to error, and a preferred approach would be to take measurements at more intensity levels than are needed just to solve for the non-linearity and DC offset parameters. It is then possible to determine the parameters using a least squares or other appropriate fitting procedure.

The net result of the calibration procedure is a number of data points representing measured voltage as a function of source intensity. This information can be stored and manipulated in a number of different ways. First, the data points can be fitted to a curve having an assumed analytic form so as to provide numerical parameter values that can then be used to solve the analytic expression. For example, in the simple case where the correction is characterized by a parameter $V_0$ corresponding to the detector voltage at zero intensity and a parameter $\alpha$ corresponding to the fixed series resistance, the parameters can be stored and the software executed at step 55 would perform the calculation of Equation 5. In a more realistic situation, the data points would likely be characterized by a larger number of correction parameters and a somewhat different analytic form of the correction.

In a particular/calibration of an MCT detector with a feedback resistor of approximately $50\Omega$, the maximum source intensity produced a measured voltage of 0.3 volts above the voltage for zero intensity. In this case, the value for $\alpha$ was determined to be 0.73, which represents a 22% correction at maximum intensity.

Calibration and Correction (AC and DC Channels)

At a given moment, the detector current includes DC and AC components corresponding to the constant and fluctuating components of the light intensity. A voltage proportional to the current is thus given by the weighted linear combination of the DC and AC channel output voltages, with the relative weighting factor determined as described above. It is this linear combination of AC and DC channel voltages that is used for the calibration and correction, as will be described below.

The interferogram, as a profile of intensity at the detector as a function of mirror position, is characterized by an average value and fluctuations about the average value. The fluctuations are largest in the centerburst region, being anywhere up to about 80% of the average value, depending on how close to ideal is the interferometer performance.

In general, the average intensity at the detector and the intensity fluctuations at the detector scale as the source intensity. For example, doubling the source intensity will double the average intensity and the fluctuations in the light reaching the detector. The scaling in the measured voltage will, however, be upset due to the detector non-linearities. Indeed, if the voltage fluctuations about the average value are large, voltage fluctuations above and below the average will scale differently from each other and from the average. Moreover, large voltage fluctuations may even cause the average value to scale differently. However, if the interferometer is intentionally put out of adjustment (detuned) so that its chopping efficiency is low, the fluctuations will be relatively small compared to the average value. The fluctuations will then scale closely as the average value, albeit non-linearly.

It is possible to perform the calibration in the same way as for the DC-coupled case, namely by illuminating the detector at various intensity levels, including zero intensity as well as levels where the detector is non-linear, and measuring the various DC channel output voltages (the AC channel output voltage should be zero for these fixed intensities). The calibration constants can then be computed as described above.

It is, however, preferred to perform the calibration with the interferometer operating. In this calibration, an adjustable source (such as a fixed source and a set of known attenuators) is passed through the interferometer, and interferograms are run with a number of source intensities. As noted above, if the interferometer is detuned, the small amplitude fluctuations in the AC channel should scale in the same ratios as the average values (relative to the DC value for zero intensity) as measured in the DC channel. This can be verified by examination and analysis of the AC and DC channel voltages.

The correction parameters can then be determined on the basis of the DC voltage ratios, alone or in combination with the AC voltage ratios (typically the ratios of peak-to-peak excursions at corresponding points in the interferograms). The subsequent correction to each point in an interferogram is computed on the basis of the linear combination of the AC and DC channel output voltages for that point, according to the equation or algorithm selected for the correction.

The process can be refined by tuning the interferometer, and using the correction parameters determined with the detuned interferometer as a starting point. An interferogram is taken with a source intensity that insures large positive excursions into the detector's non-linear range as well as large negative excursions to small intensity values. A reference interferogram is taken with a small source intensity where the detector is expected to behave linearly, or at least where the corrections are small. The correction is then applied to the interferograms, and the extent to which the two corrected interferograms scale with each other over the large and small excursions is used to form a basis for optimizing the correction parameters. It is also possible, after correcting the interferograms, to compute the spectra, and use the degree to which the spectra scale over the spectral range of interest as the basis for the optimization.

Hardware Correction

The embodiment illustrated in FIGS. 2 and 3 performs the non-linearity correction as part of the software routine that processes the digitized data values from A/D converter 35. It is, however, possible to perform the non-linearity correction before the digitized data reaches the computer. The actual correction may be done in analog or digital circuitry as will be described in greater detail below. FIGS. 5–9 are block diagrams illustrating the data acquisition and correction system in a series of embodiments of the invention where the correction for non-linearity is done in hardware. Elements corresponding to those in FIG. 2 will have the same reference numeral.

Figure 5:
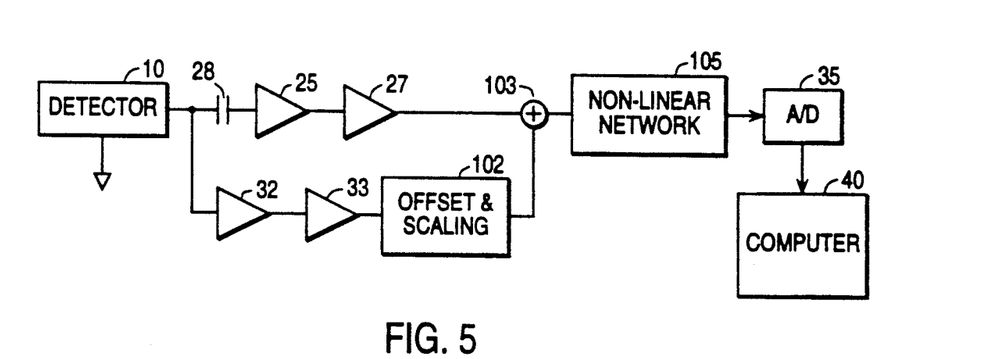
FIG. 5 is a block diagram of a dual-channel embodiment where the correction is done in hardware.

FIG. 5 is a block diagram of a dual-channel embodiment that corrects for non-linearity in hardware before digitization. As in the previous embodiment, the detector output is communicated to AC and DC channels.

The voltage from the small-bandwidth DC preamplifier (and optional DC amplifier) typically includes a DC component that is nonzero for zero intensity. This is eliminated at an offset and scaling (O/S) stage 102 so that the DC voltage is zero for zero intensity. Stage 102 may contain a further degree of amplification in addition to the offset. The DC voltage, thus offset and scaled, is linearly combined with the AC signal voltage at a summing node 103. O/S stage 102 and summing node 103 are configured to account for differences in the gains in the AC and DC channels. The result is a composite signal that represents the uncorrected total intensity (i.e., a signal proportional to the total detector current).

The output from the summing node is communicated to a non-linear network 105 that has been tailored to the non-linear characteristics of detector 10. Network 105 operates to transform the input voltage to a corrected voltage, which is then communicated to A/D converter 35 and computer 40 as described above. Since the digitized values already incorporate the non-linearity correction, the software does not perform a step corresponding to step 55 in FIG. 3.

Figure 6:
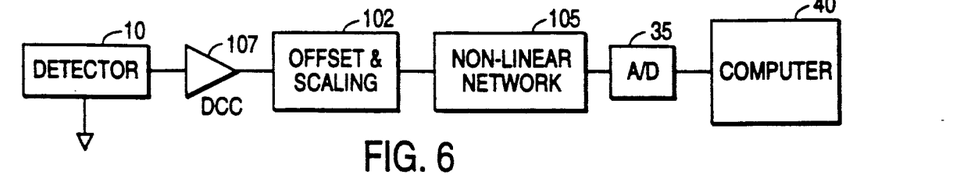
FIG. 6 is a block diagram of a single-channel embodiment where the correction is done in hardware.

FIG. 6 is a block diagram of an embodiment that uses a DC-coupled preamplifier 107 (as well as an optional amplifier) rather than the separate AC and DC channels described above. The DC-coupled preamplifier is presumed to have equal gain in a region near zero frequency and over the AC range corresponding to the spectral region of interest. The amplifier output is communicated to an O/S stage and linear network as in the dual-channel embodiment. A separate amplifier is not shown since the O/S stage may provide additional gain.

Figure 7:
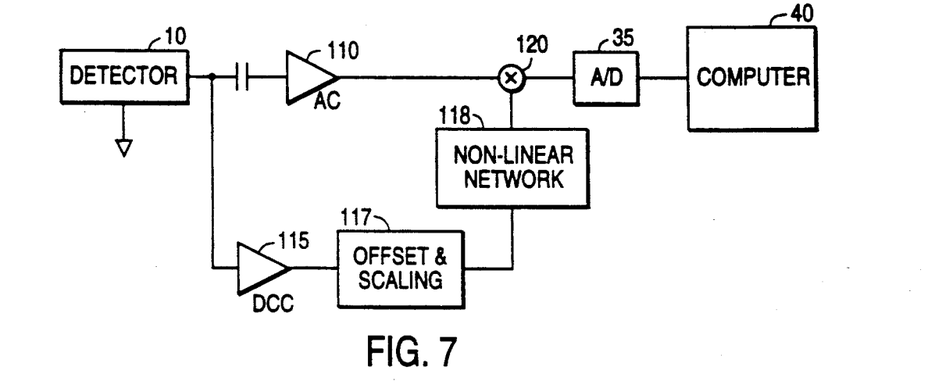
FIGS. 7 and 8 are block diagrams of dual-channel embodiments where the correction is done in hardware.

FIG. 7 is a block diagram of an embodiment that has separate AC and DC channels, develops a signal in the DC channel, and uses the signal to correct the AC signal. To this end, the signal from detector 10 is communicated to an AC preamplifier 110 and also to a DC-coupled amplifier 115 having a bandwidth that includes the frequencies of spectral interest. The output from amplifier 115 is communicated to an O/S stage 117 and a non-linear network 118. Network 118 differs from network 105 in that it transforms the input voltage to a signal that represents a correction factor that can be applied multiplicatively. This signal is applied to the signal in the AC channel at a signal multiplier 120. Signal multiplier 120 is a device having a large dynamic range so that its noise contribution is smaller than the detector noise. A possible implementation for the signal multiplier is a gain-controlled amplifier which receives the signal from non-linear network 118 at a gain-control input.

Figure 8:
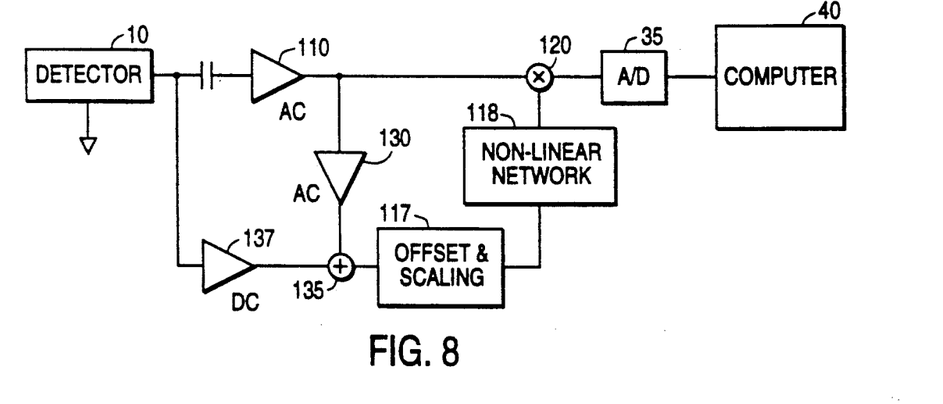

FIG. 8 is a block diagram showing a variant of the embodiment of FIG. 7. This embodiment differs in that there is no DC-coupled amplifier having a bandwidth sufficient to include DC as well as the AC frequencies of interest. Therefore, the output from AC preamplifier 110 is amplified at an AC amplifier 130 and combined at a summing node 135 with the output from a narrow bandwidth DC amplifier 137. This results in a composite signal that represents the uncorrected total intensity. Amplifier 130 and summing node 135 are configured to account for the difference in gains between AC preamplifier 110 and DC preamplifier 137. The composite signal is then treated in the same manner as the signal from DC-coupled preamplifier 115 in FIG. 7. To the extent that there is a need for the actual DC value, the output of the DC amplifier could be digitized, for example, by using a switched arrangement as shown in FIG. 2.

Figure 9:
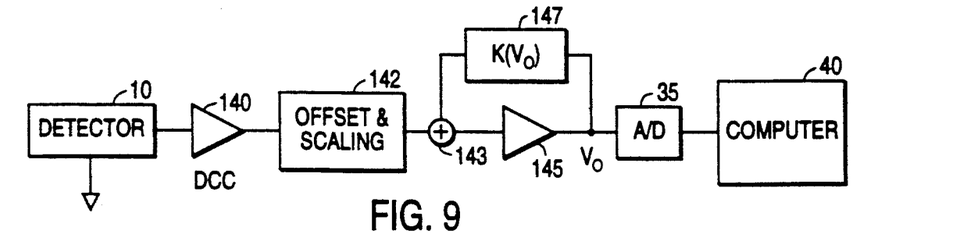
FIG. 9 is a block diagram of an embodiment with a linear preamplifier where the correction is done using positive feedback in a subsequent amplifier stage.

FIG. 9 is a block diagram showing a different hardware approach in which positive feedback is used to effect the non-linearity correction. In particular, a DC-coupled preamplifier 140 provides a signal that passes through an O/S stage 142 and is communicated to one input of a summing node 143. The output of the summing node is communicated to the input of a DC-coupled amplifier 145. The output voltage from the amplifier is communicated through a feedback network 147 to the other input of the summing node. Network 147 is tailored so that at small voltages, the amount of signal fed back is small and therefore the amplifier behaves substantially linearly. Network 147 could, for example, include a field effect transistor whose resistance varies with voltage.

At first blush, it would seem that using positive feedback in the amplifier circuit would suffer from the very noise problem discussed in connection with the prior art approach of using positive feedback in the preamplifier circuit. A simple numerical example will demonstrate that this is not the case. For purposes of this illustration, it is assumed that the detector is characterized by noise of 1 unit, the preamplifier is characterized by noise of 0.5 units at its input terminal, the preamplifier has a gain of 100, and the amplifier has the same low-noise characteristic as the preamplifier.

Under these circumstances with no positive feedback in the preamplifier, the noise in the preamplified signal would include a contribution from the detector of 100 units and a contribution from the preamplifier of 50 units. If positive feedback were introduced at this stage, the effective noise contribution of the preamplifier would also be 1 unit, so that the noise in the preamplified signal would include contributions of 100 units from each of the detector and the preamplifier. Thus the ultimate amplified signal would have as much amplifier noise as detector noise.

If positive feedback is introduced at the amplifier, the amplifier would contribute 1 unit of noise at its input terminal (not 0.5 units, since there is positive feedback). This is superimposed on detector noise of 100 units and preamplifier noise of 50 units, for a net amplifier noise contribution of 51 units. Thus the introduction of positive feedback at the amplifier has a negligible effect on the noise in the signal channel.

Figure 10:
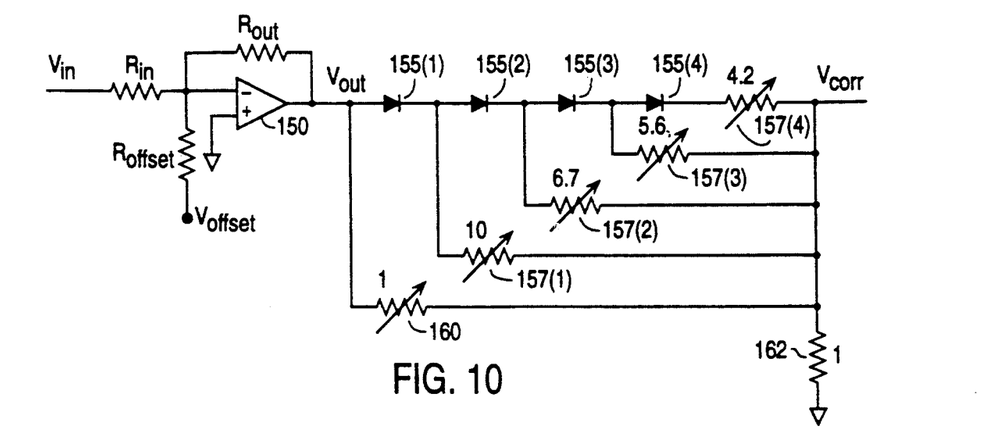
FIG. 10 is a simplified circuit schematic of analog offset, scaling, and non-linear correction circuitry.

FIG. 10 is a circuit schematic illustrating a representative construction of O/S stage 102 and non-linear network 105 when in-line as in FIG. 6. The offset and scaling portion includes an operational amplifier 150 and a resistor network. The non-inverting input of the amplifier is grounded and the inverting input is connected to three resistors. A resistor $R_{in}$ receives the input signal $V_{in}$, a resistor $R_{offset}$ communicates with an offset voltage $V_{offset}$, and a resistor $R_{out}$ provides a negative feedback connection between the output terminal and the non-inverting input terminal. Thus, the output voltage $V_{out}$ from the operational amplifier is given by the following formula.

$$V_{out} = -(R_{out}/R_{in})V_{in} - (R_{out}/R_{offset})V_{offset}$$

Thus, it is possible to provide any desired degree of offset and scaling by suitable choices of the resistors and offset voltage. $V_{out}$ is a voltage that exhibits the non-linear characteristic such as that shown by $V_{meas}$ in FIG. 1B.

A representative non-linear network comprises a diode-resistor structure defined by diodes 155(1) through 155(4) and resistors 157(1) through 157(4), and 160 and 162. The approximate values of the resistors are shown, but at least some of the resistors are shown as variable resistors. This is because they are adjustable, with the adjustment being performed during calibration. The network receives voltage $V_{out}$, which is assumed to be positive for nonzero intensity and zero for zero intensity, across the voltage divider and provides a voltage $V_{corr}$ at the intermediate node of the voltage divider. The diode-resistor structure is connected across resistor 160.

The operation of the non-linear network may be summarized as follows. For small values of $V_{out}$, none of the diodes conducts, and $V_{corr}$ is determined by the ratio of resistors 160 and 162. When $V_{out}$ reaches the level necessary to turn a diode on, diode 155(1) begins to conduct and provides an additional conduction path through resistor 157(1). This changes the effective ratio of the voltage divider so that $V_{corr}$ becomes a greater fraction of $V_{out}$. Similarly, when $V_{out}$ reaches the level sufficient to turn diodes 155(1) and 155(2) on, an additional current path is established through resistor 157(2). Thus, as $V_{out}$ increases, additional current paths are established, and $V_{corr}$ becomes a greater fraction of $V_{out}$.

Figure 11:
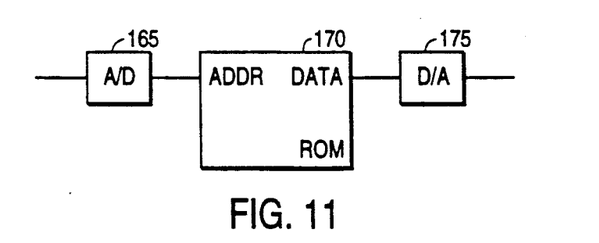
FIG. 11 is a block diagram of a ROM-based correction network.

FIG. 11 shows an alternative non-linear network. The voltage is communicated to an A/D converter 165, the digitized output of which is communicated to the address inputs of a ROM chip 170. The ROM data output is communicated to the input of a D/A converter 175, the analog output of which is a voltage having the desired functional dependence on the input voltage. When this approach is used in connection with an embodiment such as shown in FIGS. 7 and 8, the voltage is communicated to the relevant multiplication node. Since the DC voltage component corresponding to zero intensity was eliminated, better use is made of the A/D converter's range. The ROM may be a 256×16 EPROM. When this approach is used in connection with an embodiment such as shown in FIGS. 5 and 6, D/A converter 175 and A/D converter 35 are not necessary. In such a case, A/D converter 165 would require more bits and ROM 170 would need to be larger to provide the necessary precision.

The values stored in the ROM are determined by the detector calibration and the properties of the signal multiplier (if applicable). Since the detector and its associated electronics (preamplifiers) constitute a unit, it is convenient to have the gain control circuitry on the same circuit board, and program the ROM at the time of performing the calibration. Indeed, even for a software embodiment, it may be appropriate to have calibration information 45 stored in a ROM that is located on the circuit board that contains the detector electronics.

Figure 12:
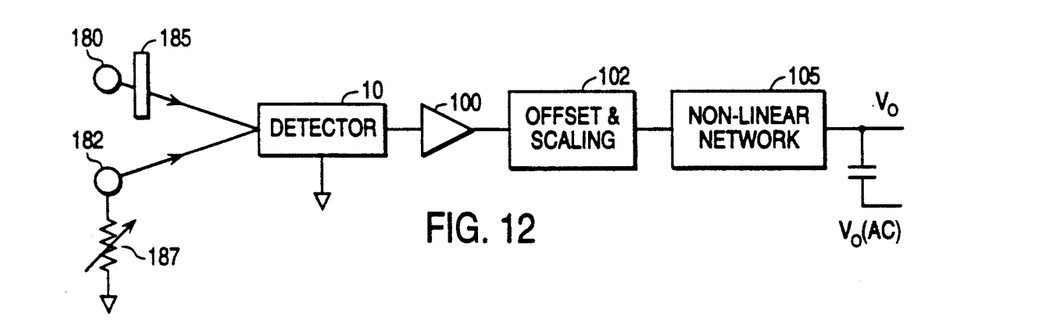
FIG. 12 is a block diagram of apparatus for calibration.

FIG. 12 shows apparatus for calibrating non-linear network 105, which was described in connection with the embodiments of FIGS. 5 and 6. The calibration apparatus includes a low-intensity light source 180 (intensity low enough that the detector is linear) and a light source 182 having an adjustable intensity up to the maximum level expected. Thus, source 182 is expected to provide intensities where the detector is non-linear. A chopper 185 is interposed between source 180 and the detector. Initially, both sources are set for zero output, and the parameters of O/S stage 102 are set for zero output voltage. Source 180 is then energized at a fixed low intensity that is less than the value where non-linearity is expected to occur. This intensity is maintained at a constant level during the calibration. The chopper is activated and the AC component of the output voltage is measured. The intensity of source 182 is then increased in steps, and at each step, the AC component of the output voltage is measured, and the parameters of non-linear network 105 are adjusted so as to make the AC voltage equal to the value that it had for zero intensity of source 182.

Approximate Correction Techniques

The various techniques described above attempt to correct the detector voltage at each point on the interferogram by a correction factor appropriate to the total intensity at that point. As discussed above, this typically requires accurate measurements of the AC and DC components. It is possible, however, to provide approximate corrections that are still useful, since some correction is likely to be better than no correction at all.

One approach is to forego the point by point correction, and merely scale the interferogram (or the spectrum) by a correction factor based on the average value as provided by the DC channel. To the extent that the fluctuations of the interferogram about the average value are not too large, the correction factor that should be applied to each point does not vary appreciably over the interferogram except in the centerburst region. Thus, it is possible to perform an approximate correction by applying a single correction factor (based on the average interferogram value) to each point. This tends to correct the spectral amplitudes (i.e., the height of the spectrum), although spurious effects still tend to remain. Since many spectral investigations are primarily concerned with the ratio of a spectrum to a reference spectrum, a correction at this level may be all that is needed. It may seem of questionable value, however, to have the program perform a degraded version of the correction, since the computation time for the correction does not significantly impact the overall data processing throughput. Nevertheless, the approximate correction has the advantage that it can be easily implemented in hardware.

A second approach is to relax the requirement that the average value of the interferogram be known precisely. As noted above, the maximum peak-to-peak excursion in the interferogram is related to the average value in a manner that depends on the chopping efficiency of the interferometer. By way of a simplified example, if the chopping efficiency were 100%, the average value would be 50% of the maximum peak-to-peak excursion. Thus, it is possible to eliminate the separate DC channel and derive the average value from the AC channel.

According to this embodiment, the chopping efficiency of the interferometer is determined and is made part of the calibration information associated with the particular instrument. The chopping efficiency of an instrument having only an AC channel can be determined at the factory by temporarily providing a DC amplifier and making AC and DC measurements with the instrument. Alternatively, such measurements can be made on a few of the same model of instrument, and numerical values derived that can be used on all instruments of that model. If the correction is to be done in software, which is most likely for this case, the wavelength dependence of the chopping efficiency can be incorporated into the calibration information.

Prior Art AC Preamplifier

Figure 13A:
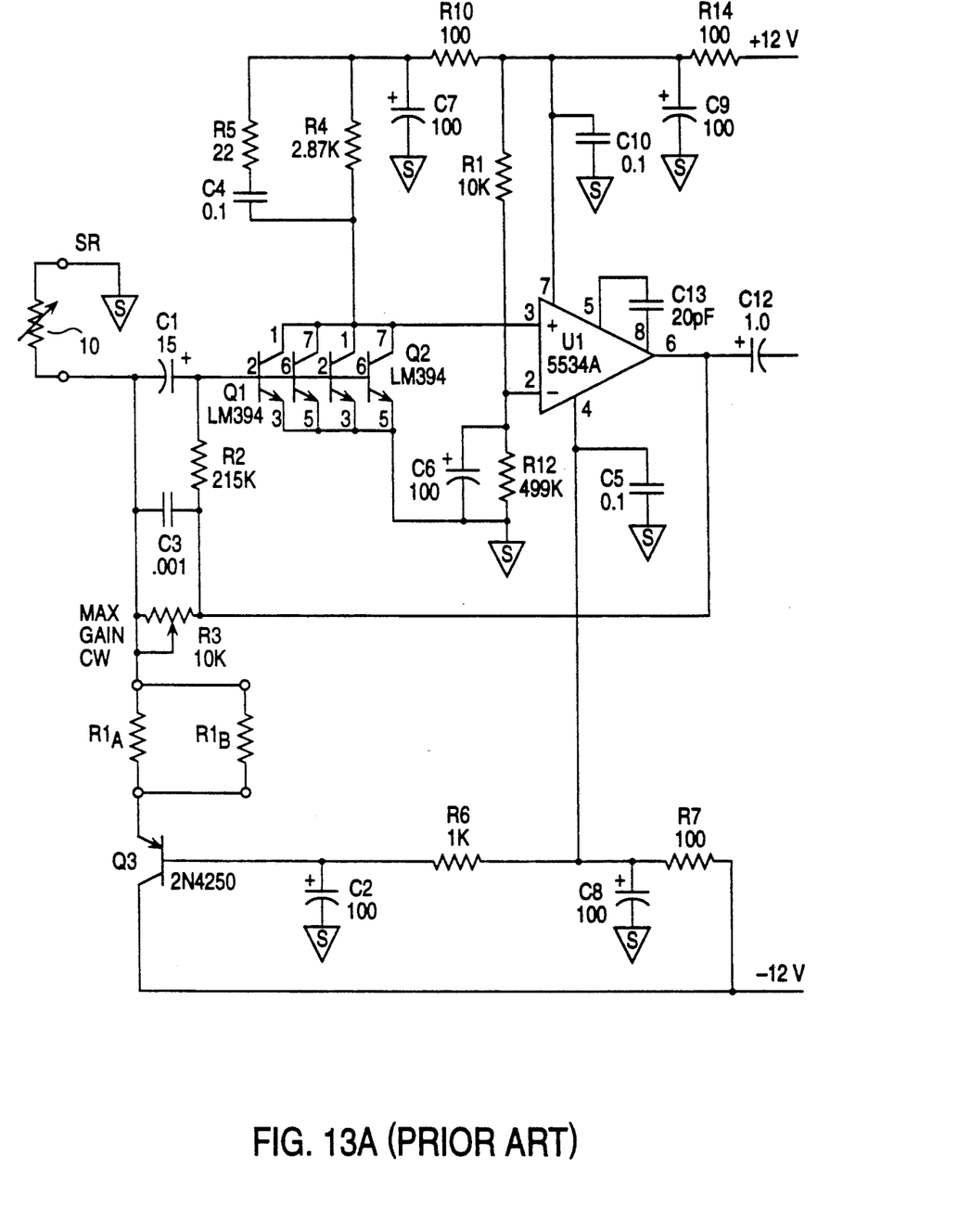
FIGS. 13A and 13B, taken together, provide a circuit schematic of a prior art embodiment of an AC-coupled preamplifier.
Figure 13B:
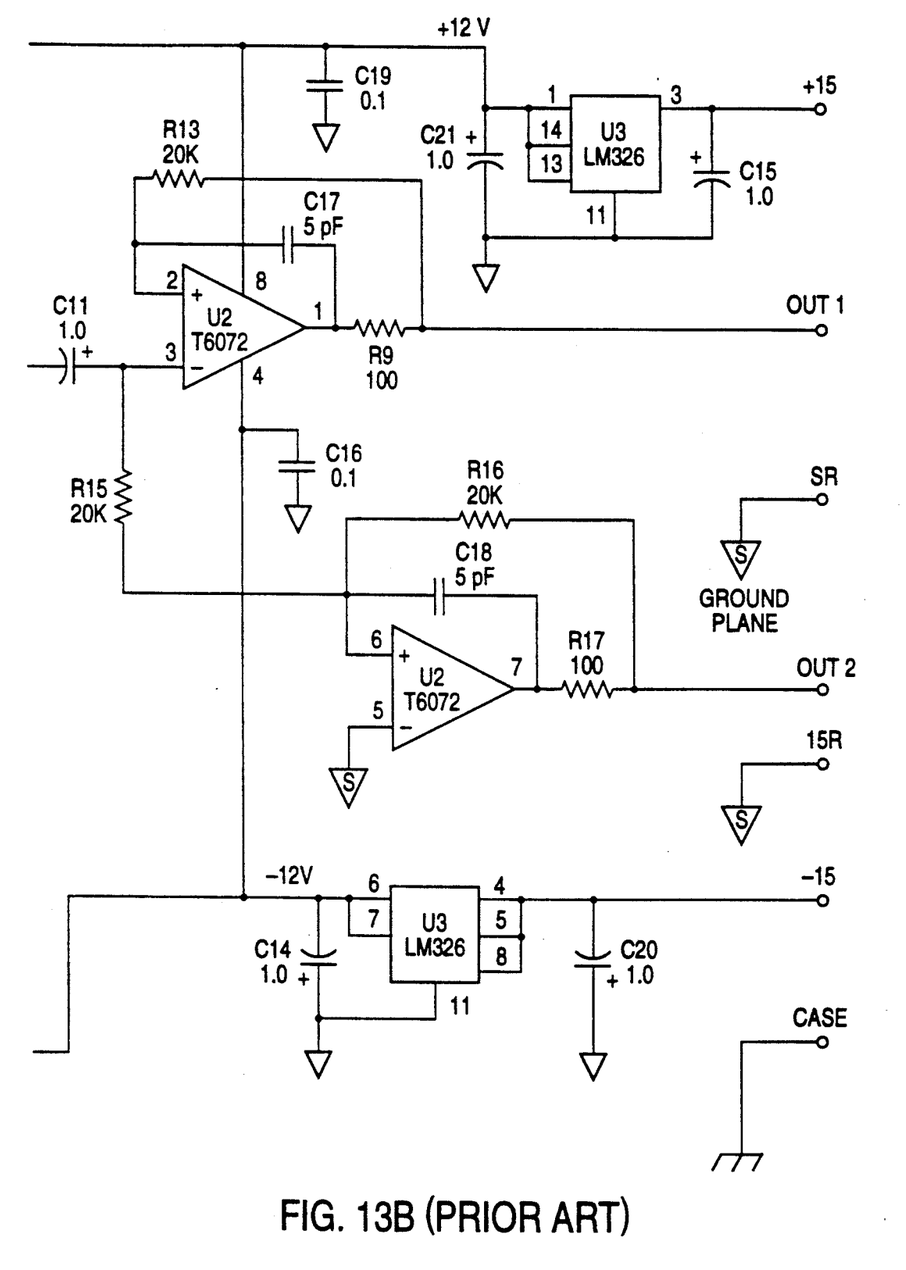

FIGS. 13A and 13B, taken together provide a circuit schematic of a prior art AC-coupled preamplifier circuit used with mercury cadmium tellurium (MCT) photodetectors. This type of circuit represents the preferred approach for the AC channel. However, the bias circuit for the system of FIG. 4 has to provide a constant detector voltage, which is not the case for this prior art preamplifier.

A bias current is supplied through bias resistors R1A and R1B, while a transistor $Q_3$, a capacitor C2 and a resistor R6 provide an active filter for this bias current. Unlike the DC-coupled case, the DC voltage on the detector is not maintained at a constant value.

Amplification with negative feedback is provided by an input AC gain stage (Q1, Q2) and an operational amplifier U1. Since the gain stage inverts, the signal is communicated to the non-inverting input terminal of amplifier U1. Feedback resistors R2 and R3 are coupled between the output terminal of amplifier U1 and a blocking capacitor C1. The use of these two resistors allows capacitor C1 to be smaller than it would otherwise have to be if a single feedback resistor were used. Resistor R3 can be varied to adjust the overall gain of the preamplifier.

The signal from amplifier U1 is communicated through blocking capacitors C12 and C11 to the inverting and non-inverting input terminals of a pair of operational amplifiers U2, which are used as a buffer to provide a balanced output signal. The output signal is provided on a pair of conductors with a single shield so as to reject common-mode noise. The input gain stage optimizes the noise performance of the amplifier for low impedance detectors (the impedance of MCT detectors is on the order of 10–100Ω), but is not necessarily optimized for low drift.

Conclusion

In conclusion, it can be seen that the present invention provides a self-consistent way to calibrate a spectrometer to account for non-linearity of the detector response. The correction can be done in hardware or software. Once the calibration procedure has been carried out and the relevant parameters stored for the software embodiment, the correction presents minimal computational penalty and allows the best measurement to be obtained.

While the above is a complete description of a number of embodiments, various modifications, alternatives, and equivalents may be used. For example, while the calibration and correction techniques were described above in the context of photoconductive detectors such as MCT, the invention applies to other types of photodetectors that might exhibit non-linear behavior. Additionally, rather than storing the correction information as parameters for an analytic computation, it is possible to store a set of data points representing the correction in a table, and to determine the correction for a particular measured voltage by linear or non-linear interpolation.

Therefore, the above description should not be taken as limiting the scope of the invention which is defined by the appended claims.

What is claimed is:

1. A method of acquiring interferogram data in a Fourier transform spectrometer, the spectrometer including a detector that provides an output signal that exhibits a non-linear variation as a function of intensity, comprising the steps of:
   providing calibration information representing the non-linear variation;
   coupling the detector to a preamplifier circuit characterized by the absence of positive feedback to provide a preamplified output signal representing the intensity;
   operating the spectrometer to modulate the intensity; and
   converting the preamplified output signal to a set of digitized values that have been corrected in accordance with the calibration information;
   said providing step being performed before and independently of said operating step.

2. The method of claim 1 wherein the preamplified output signal includes DC and AC components.

3. The method of claim 1 wherein:
   the preamplified signal includes a DC and AC components; and
   the DC and AC components are provided in separate channels.

4. The method of claim 1 wherein the preamplified output signal includes an AC component only, the AC component at a given time being characterized by a peak-to peak excursion, and where an average value is determined on the basis of the maximum peak-to-peak excursion of the AC component.

5. The method of claim 1 wherein said converting step includes the substeps, carried out in the order stated, of:
   coupling the preamplified output signal to an amplified circuit characterized by the absence of positive feedback to provide an amplified output signal;
   digitizing the amplified output signal to provide measured values representing uncorrected intensity information; and
   correcting each measured value using the calibration information to provide a corrected value.

6. The method of claim 5 wherein the amplified output signal includes DC and AC components, and each measured value represents a liner combination of the DC and AC components.

7. The method of claim 5 wherein the preamplified signal includes DC and AC components, the DC and AC components are provided in separate channels, and said digitizing step is carried out on signals representing the AC and DC components separately, and further comprising the step, carried out before said correcting step, of linearly combining the digitized AC and DC values.

8. The method of claim 1 wherein said converting step includes the substeps, carried out in the order stated, of:
   correcting the preamplified output signal using the calibration information to provide a corrected signal; and
   digitizing the corrected signal to provide a set of corrected values.

9. The method of claim 1 wherein said converting step includes the substeps, carried out in the order stated, of:
- coupling the preamplified signal to an amplifier circuit having a positive feedback portion representing the calibration information to provide a corrected signal; and
- digitizing the corrected signal to provide a set of corrected values.

10. In the operation of a Fourier transform spectrometer, a method of correcting for detector non-linearity comprising the steps of:
- providing calibration information representing the non-linearity;
- simultaneously measuring AC and DC components of the detector signal;
- determining a correction factor on the basis of at least the calibration information and the measured DC component; and
- applying the correction factor to the AC component; said providing step being performed before and independently of said measuring step.

11. The method of claim 1 or 10 wherein the detector is an MCT detector.

12. A method of calibrating a detector in a Fourier Transform spectrometer, the detector providing an output signal that exhibits a non-linear variation as a function of intensity, comprising the steps of:
- coupling the detector to a preamplifier circuit characterized by the absence of positive feedback to provide a preamplified output signal representing the intensity;
- coupling the output signal to an adjustable non-linear network having an output terminal;
- providing a first light source characterized by an intensity that exhibits fluctuations about an average value where the amplitude of the fluctuations and the average value are small compared to a defined maximum;
- providing a second light source having an adjustable intensity capable of assuming values between zero and the defined maximum, the intensity, once adjusted, being constant;
- illuminating the detector with only the first source operating at a reference intensity, and measuring the AC component of the voltage at the output terminal of the non-linear network, the measured value being designated a reference value; and
- illuminating the detector with both sources at each of a set of conditions with the first source operating at the reference intensity and the second source adjusted to provide a different intensity for each condition, and for each condition, adjusting the non-linear network so that the AC component of the voltage at the output terminal of the non-linear network is equal to the reference value.

13. A method of calibrating a detector in a Fourier transform spectrometer, the detector providing an output signal that exhibits a non-linear variation as a function of intensity, the spectrometer including an interferometer and circuitry for generating an uncorrected detector signal, comprising the steps of:
- generating a plurality of interferograms at a corresponding plurality of different illumination conditions, the illumination conditions having a known relationship to each other, the spectrometer being adjusted for low chopping efficiency so that the interferograms exhibit fluctuations that are a small fraction of the average value of the interferogram;
- measuring corresponding values of the detector signal for each of the interferograms; and
- correlating the measured detector signal values and the known relationship to determine calibration information representing the non-linear variation.

14. The method of claim 13 wherein the different illumination conditions are established using a source operated at fixed conditions with one or more attenuators of known characteristic.

15. The method of claim 13 wherein the corresponding values of the detector signal are the average values of the detector signal.

16. The method of claim 13 wherein the corresponding values of the detector signal are the average values and at least some values of peak-to-peak excursions of the detector signal.

17. The method of claim 12 or 13 wherein the detector is an MCT detector.

18. The method of claim 13, and further comprising the steps of:
- measuring the detector signal value for zero intensity; and
- using the value, so measured, in said correlating step.

19. A Fourier transform spectrometer comprising:
- a detector that provides an output signal that exhibits a non-linear variation as a function of intensity;
- a preamplifier circuit, responsive to the output signal and characterized by the absence of positive feedback to provide a preamplified output signal representing the intensity;
- an amplifier circuit, responsive to the preamplified signal, and including a positive feedback element having a voltage-dependent characteristic representing the non-linear variation to provide an amplified output signal that exhibits a variation as a function of intensity that is more linear than the variation exhibited by the detector output signal; and
- means for digitizing the amplified output signal to provide measured values representing corrected intensity information.

20. A Fourier transform spectrometer comprising:
- a detector that provides an output signal that exhibits a non-linear variation as a function of intensity;
- means for providing predefined calibration information representing the non-linear variation;
- an amplifier circuit, responsive to the output signal and characterized by the absence of positive feedback to provide an amplified output signal representing the intensity;
- means for modulating the intensity; and
- means for digitizing the amplified output signal to provide measured values representing uncorrected intensity information; and
- means for correcting each measured value using the predefined calibration information to provide a corrected value.

21. The Fourier transform spectrometer of claim 20 wherein the amplifier circuit includes separate AC and DC channels that provide respective AC and DC components of said amplified output signal, and said means for digitizing operates on said AC and DC components separately, and further comprising means for linearly combining the AC and DC components, so digitized.

22. The Fourier transform spectrometer of claim 20 wherein the amplifier circuit is DC-coupled.

23. A Fourier transform spectrometer comprising;
 a detector that provides an output signal that exhibits a non-linear variation as a function of intensity;
 means for providing predefined calibration information representing the non-linear variation;
 means for measuring AC and DC components of the detector signal;
 means for determining on the basis of the predefined calibration information and a predetermined linear combination of the measured AC and DC components a correction factor appropriate for the measured linear combination; and
 means for applying the correction factor to the measured linear combination.

24. In a Fourier transform spectrometer, apparatus for correcting the AC signal for detector non-linearity comprising:
 means defining an AC signal channel having a controllable gain;
 means defining a DC signal channel;
 means for providing predefined calibration information regarding the detector non-linearity; and
 means, responsive to at least the predefined calibration information and signals in the DC channel, for changing the gain in the AC channel to provide at least a partial correction.

25. The Fourier transform spectrometer of claim 20 or 23 or 24 wherein the detector is an MCT detector.

26. The Fourier transform spectrometer of claim 20 or 23 or 24, wherein the means for providing predefined calibration information comprises a non-linear network.

27. The Fourier transform spectrometer of claim 26 wherein the non-linear network comprises a non-linear circuit element.

28. The Fourier transform spectrometer of claim 26 wherein the non-linear network comprises a read-only memory containing a table that maps an uncorrected digital value to a corrected digital value.

* * * * *